United States Patent [19]

Malenchek

[11] Patent Number: 5,437,639
[45] Date of Patent: Aug. 1, 1995

[54] NEEDLE PROTECTIVE SHEATH DEVICE

[76] Inventor: Robert Malenchek, 279 Sunnymead Rd., Somerville, N.J. 08876

[21] Appl. No.: 308,386

[22] Filed: Sep. 19, 1994

[51] Int. Cl.⁶ ............................................. A61M 5/00
[52] U.S. Cl. ................................. 604/110; 604/198; 128/763
[58] Field of Search ............... 604/110, 187, 198, 263, 604/195; 128/763, 764, 765

[56] References Cited
U.S. PATENT DOCUMENTS

| | | | |
|---|---|---|---|
| 4,840,185 | 6/1989 | Hernandez | 128/763 |
| 4,915,702 | 4/1990 | Haber | 604/198 |
| 5,067,490 | 11/1991 | Haber | 604/110 |
| 5,356,392 | 10/1994 | Firth et al. | 128/763 X |

*Primary Examiner*—John D. Yasko
*Attorney, Agent, or Firm*—Omri M. Behr; Matthew J. McDonald

[57] ABSTRACT

An inner cylindrical member has a pair of opposing axially extending tapered slots extending toward an end distal the other proximal end to which a needle is secured for blood collecting. A pair of tabs protrude from the distal end to permit the member sides at the distal end to be squeezed together. Temporary locking projections on the inner member sides at the distal end are engaged with locking holes on an outer nested concentric cylindrical member. The squeezing action releases the temporary locking engagement. Other projections and locking ramps are on the inner member at the proximal end for engaging the locking holes on the outer member. Guide channels are in the outer member inner wall engaged with the inner member proximal projections and ramps for guiding these elements as the outer member is axially displaced from a needle use mode overlying the inner member to a needle protection mode cantilevered from the inner member.

16 Claims, 3 Drawing Sheets

NEEDLE PROTECTIVE SHEATH DEVICE

This invention relates to needle protective sheath devices, more particularly, protective devices used to protect hypodermic and blood collecting needles.

Needle protective sheath devices are in wide use. They typically comprise inner and outer cylindrical members with mating locking ribs and grooves and similar locking devices. The locking ribs and grooves temporarily lock the outer protective sheath in a first mode wherein the needle is exposed and projects from the protective device. This locking position is to preclude the members from accidentally engaging their locking devices in a permanent needle protective locking position prior to use of the needle. The device may be of the type for receiving a plunger in a syringe in a hyperdermic application or a vacuum cartridge having a septum which is penetrated by a needle portion inside the bore of a receiving cylinder in a blood collecting application. A blood collecting needle portion projects beyond the cylinder. When its use is completed the outer cylinder member is axially displaced from an overlying position with the inner member to a position cantilevered from the inner member and locked into a needle protective position.

The problem recognized by the present invention is that the prior art devices tend to be permanently locked in the needle use mode which is intended to be temporary. This is because the locking means for the temporary mode tend to be similar in construction as the locking means for the permanent needle protective mode. Therefore, it sometimes may be relatively difficult to disengage the inner and outer cylinder members for placement into the needle protective mode.

In accordance with an embodiment of the present invention, a needle protective sheath device comprises a first cylindrical member having an axially extending bore extending therethrough and terminating at distal and proximal end edges of the member, the member having an axially extending slot on opposite sides thereof so the distal end edges can be manually squeezed together. First locking means are on an outer surface of the member adjacent to the distal end. Second locking means are on the outer surface adjacent to the proximal end.

A second cylindrical member has an axially extending bore extending therethrough and terminating at distal and proximal member ends for receiving the first member therein in nested concentric relation, the second member having third locking means at the distal end thereof releasably engaged with the first locking means with the members overlying each other in the nested relation in a first relative position, the third locking means being released from engagement with the first locking means upon the squeezing the distal end edges and for locking engagement with the second locking means in a second relative position wherein the second member extends cantilevered from the first member in a needle protective condition.

In a further embodiment, the second member has at least one axially extending channel in the wall forming the bore thereof, the first member including at least one axially extending ramp engaged with the channel, the channel for guiding the ramp in the axial direction, the ramp forming fourth locking means for locking the distal edge of the first member in the axial direction.

In a still further embodiment, the first and second locking means are projections extending from the peripheral outer surface of the first member and the third locking means is at least one aperture for selectively receiving the projections.

Figure 1:
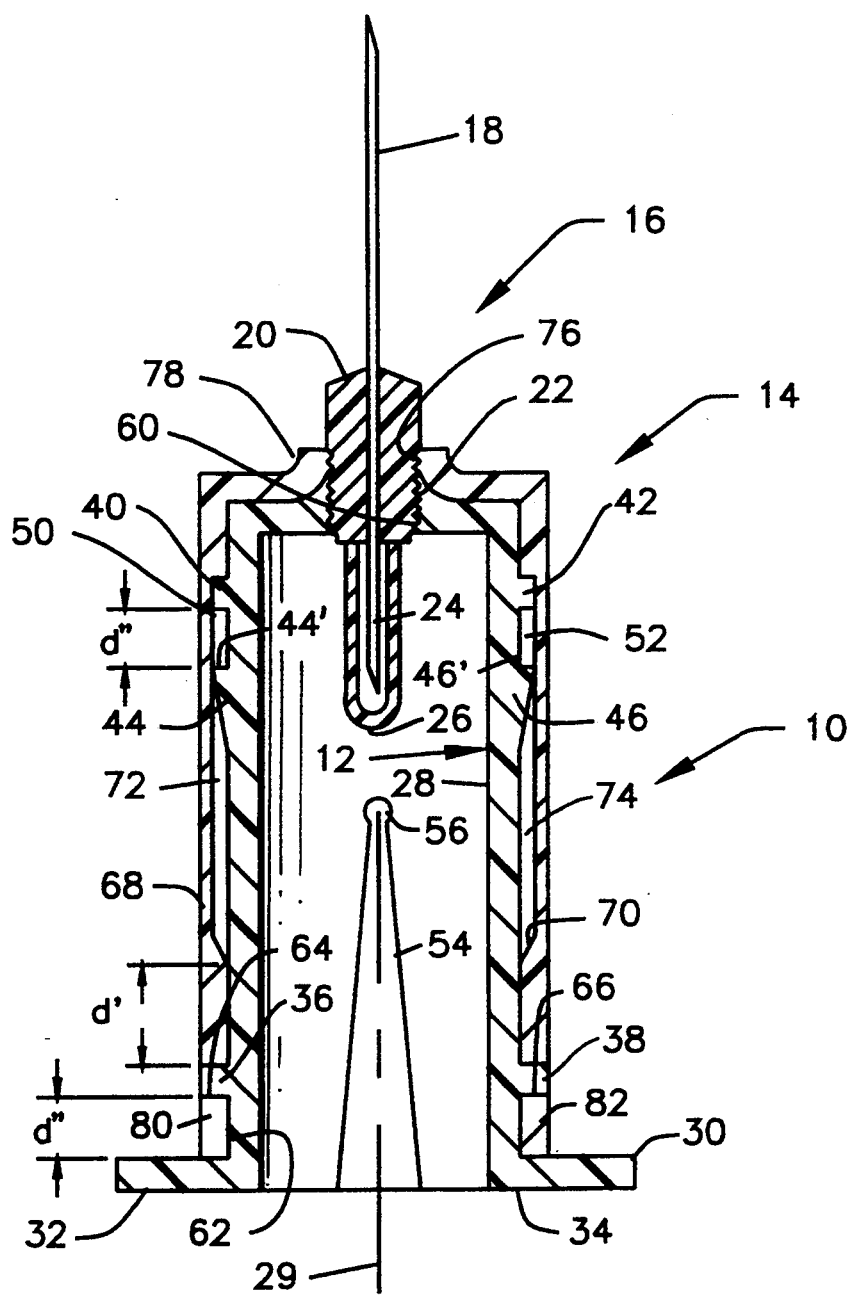
FIG. 1 is a side elevation sectional view of a blood collecting device in a needle use mode (without the blood collecting cartridge inserted) according to one embodiment of the present invention.

In FIG. 1, device 10 comprises an inner cylindrical thermoplastic molded member 12 and an outer cylindrical thermoplastic molded member 14. The members are preferable thermoplastic but could be other materials. In this embodiment the device 10 is employed for blood collecting using a vacuum cartridge (not shown) as commonly employed in this field, but could be used in a syringe implementation if desired. A needle assembly 16 is attached to the inner member 12.

The needle assembly 16 comprises a hollow needle 18 secured to a thermoplastic connector 20. The connector 20 has threads 22. The needle 18 has a portion 24 which extends beyond the connector 20. A soft protective rubber cover 26 is secured to connector 20 and extends over the needle portion 24. When the septum of a blood collecting cartridge is forced against the cover 26, the needle portion 24 penetrates the cover 26 and the cartridge septum in conventional fashion to engage the bore of the cartridge.

Inner member 12 comprises a circular cylindrical sleeve 28 having a bore extending along and concentric with longitudinal axis 29. The sleeve 28 has outwardly radially extending tabs 30 and 32 at distal edge 34 relative to the needle 18. A pair of like circular radially outwardly extending aligned projections 36 and 38 project from the outer periphery surface of the sleeve 28 in a region adjacent to the distal end at edge 34. While two projections are shown more or fewer may be provided in the alternative. In a further alternative the projections may comprise circumferential ribs (not shown). A further pair of like circular cylindrical projections 40 and 42 extend radially outwardly from the outer periphery surface of the sleeve 28. The projections 40 and 42 are shorter in length than projections 36 and 38 for reasons to be explained. The projections 40 and 42 are adjacent the end of the sleeve opposite distal edge 34 and are proximal the needle 18.

A pair of ramps 44 and 46 of like dimensions project from the outer surface of the sleeve 28 axially spaced toward the distal end relative to the projections 40 and 42. The ramps incline radially outwardly as they approach the projections 40 and 42 toward the proximal end of the sleeve 28. The ramps extend radially outwardly about the same distance as the projections 40 and 42. The projections 40 and 42 are spaced from the respective corresponding ramps 44 and 46 a distance d" which is preferably about the same spacing d" as the projections 36 and 38 from respective tabs 32 and 34. The ramps 44 and 46 each have a shoulder 44'0 and 46' respectively which is normal to the axis 29 and parallel to the sides of projections 40 and 42 defining respective annular groove segments 50 and 52 therebetween.

A pair of tapered slots 54 (one being shown) are in opposite sides of the sleeve 28 medially between the projections 36 and 38. The slots 54 medially along the axis of the sleeve 28 from a circular aperture 56 to distal edge 34 of member 12. The slots 54 taper from a narrow spacing at aperture 56 to a wider spacing at edge 34.

The proximal end of the member 12 has a reduced cross section area threaded opening 60. Opening 60 receives the threads 22 of connector 20 for attaching the needle 18 to the proximal end of the member 12. The needle 18 bore is in communication with the bore of the cover 26 and thus the bore of sleeve 28 when portion 24 penetrates the cover 26. Not shown is a temporary protective cover for the needle 18 prior to its attachment to the member 12.

The outer member 14 has a bore 62 which is closely received over the outer surface of the inner member sleeve 28. A pair of like circular cylindrical diametrically opposite holes 64 and 66 closely receive respective projections 36 and 36 When axially aligned therewith as shown in FIG. 1. Spaced distance d' from holes 64 and 66 are respective ramps 68 and 70 which terminate in longitudinally axially extending channels 72 and 74, respectively. Channel 72 receives ramp 44 and projection 40 and channel 74 receives ramp 46 and projection 42. The channels axially guide the respective ramps and projections therein.

Figure 3:
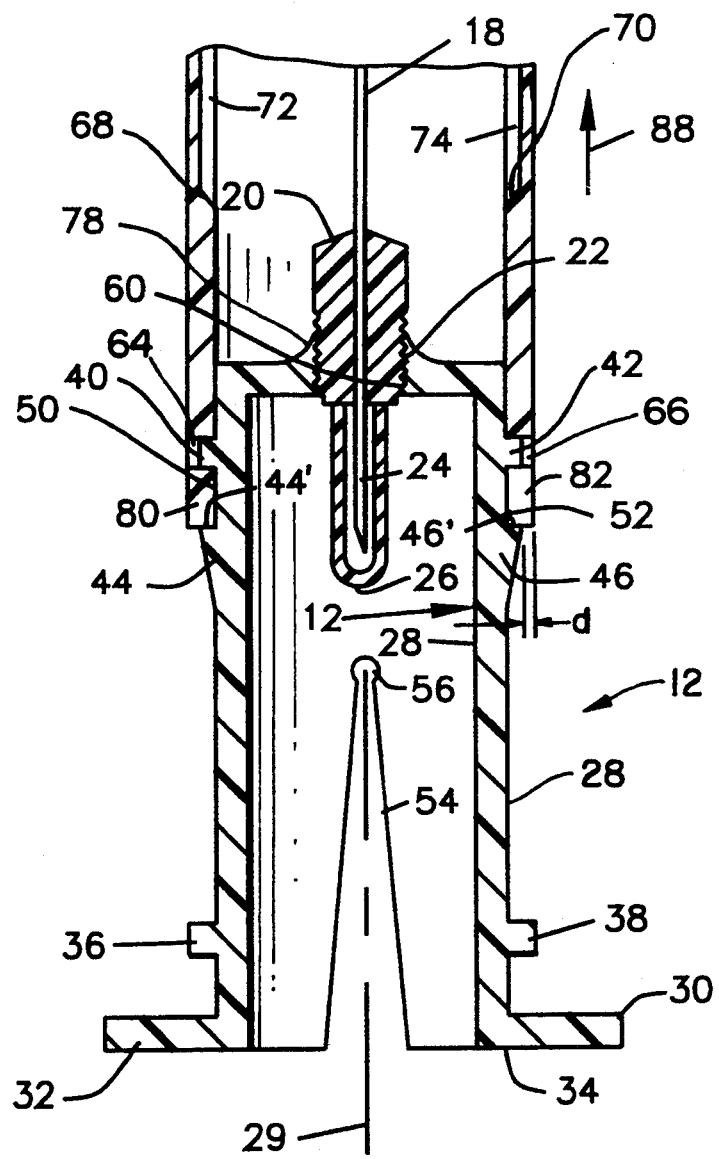
FIG. 3 is a side elevation sectional fragmented view of the device of FIG. 1 locked in a needle protective mode.

The proximal end of the cylinder 14 adjacent to needle 18 terminates in a reduced diameter opening 76 for closely receiving connector 20. Also, the member 14 has a spout-like projecting end 78 forming opening 76. The cylinder member 14 has a portion 80 between hole 64 and its distal edge at tab 32 and a portion 82 between hole 66 and the distal edge at tab 30. Portions 80 and 82 have an axial extent parallel to axis 29 distance d". Distance d" is arranged to be such that portion 80 of the outer member will fit in the space between projection 40 and shoulder 44' of ramp 44 and member 14 portion 82 will fit in the space between projection 42 and shoulder 46' of ramp 46. In this latter position the portions 80 and. 82 are axially locked in place in the needle protective mode of FIG. 3.

In operation, in FIG. 1, the needle 18 is assembled to the inner member 12 via connector 20. At this time the outer member 14 is locked to the inner member as shown with the distal ends of the inner and outer members overlying one another and with the proximal ends overlying one another. The locking occurs with the projection 36 engaged with hole 64 and the projection 38 engaged with hole 66. In this needle use mode the needle 18 extends from the concentric overlying members 12 and 14. A cartridge (not shown) is inserted in the bore of the two combined members with the septum of the cartridge penetrated by needle portion 24. The needle 16 is inserted for blood collection and when done, the cartridge is removed from the members 12 and 14.

Figure 2:
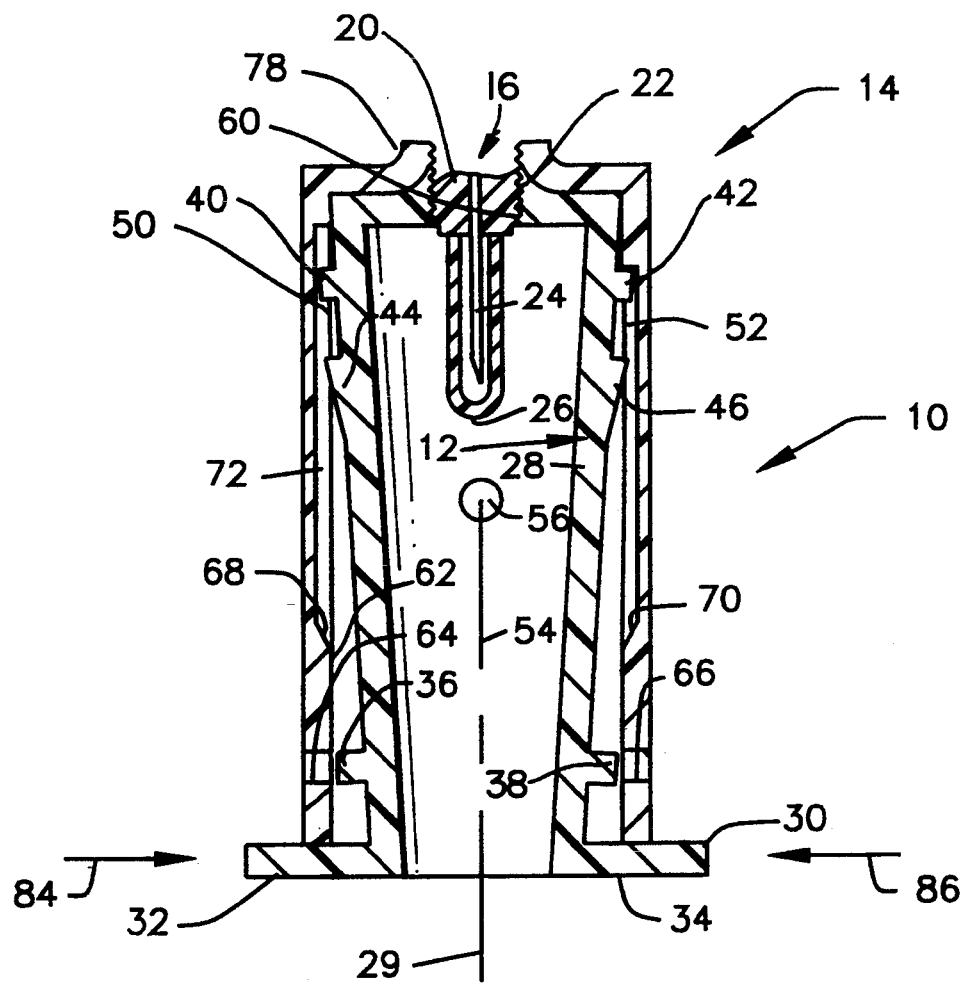
FIG. 2 is a side elevation fragmented sectional view similar to that of FIG. 1 in which the temporary locking means are disengaged prior to placement of the protective sheath in a needle protective position.

In FIG. 2, the tabs 30 and 32 are squeezed together in the direction of respective arrows 84 and 86 until the edges of the slot 54 abut as shown. At this time the projections 36 and 38 are disengaged from the holes 64 and 66. Subsequently, in FIG. 3 the outer member 14 is slid axially in direction 88. In so sliding, the channels 72 and 74 guide the ramps 44 and 46 until they engage ramps 68 and 70 spreading the sides of the outer member 14 apart. The member 14 is further axially slid in direction 88 until the portions 80 and 82 snap into the groove segments 50 and 52 and the projections 40 and 42 engage the holes 64 and 66. In this position the outer member is locked axially in place by the locking action of the shoulders 44' and 46'. It will be apparent that while in this embodiment the channels terminate at ramps 68 and 70, further shallower channels, not shown, may extend from ramps 68 and 70 to the distal end edge of the outer member 14 to guide the projections 40 and 42 into engagement with the holes 64 and 66, FIG. 3. The shallower channels are provided to implement the ramping of the member 14 distal end over the projections 40 and 42 while providing alignment therewith.

The projections, holes and ramps may be placed on reversed respective members according to a given implementation. Also the projections and holes may be replaced by ribs and grooves. Other modifications may be made by one of ordinary skill. It is intended that the detailed description be illustrative and not limiting. The scope of the invention is as defined in the appended claims.

What is claimed is:

1. A needle protective sheath device comprising:

a first cylindrical member having a first cylindrical cavity defining a longitudinal axis, said member having proximal and distal ends, said member having first and second openings on and extending radially transverse the axis in communication with the cavity on the respective distal and proximal ends, the second opening on the proximal end being restricted in transverse dimension with respect to the first opening on the distal end, the member including means at the proximal end opening for securing a needle thereto in communication with the cavity, the secured needle extending axially beyond the first member proximal end, the member including finger gripping means on the distal end, said member having a pair of opposed axially extending slits in communication with the distal end arranged such that opposing sides of the distal end can be squeezed together from a normally spaced apart position to a compressed position;

first locking means on the member outer surface external the cavity on each said opposing sides adjacent to said distal end;

second locking means on the member outer surface external the cavity adjacent to said proximal end;

a second cylindrical member having a second cylindrical cavity defining a second longitudinal axis, said second member having proximal and distal ends, said second member having third and fourth openings on and extending radially transverse the second axis in communication with the second cavity at the respective distal and proximal ends, the fourth opening on the proximal end being restricted in transverse dimension with respect to the third opening on the distal end, said second cavity for axially receiving the first member through the third opening with the first and second members in nested concentric relation in a first axial relative position with the members overlying one another with their respective proximal and distal ends adjacent to each other and in a second extended position wherein the second member distal end is adjacent to the first member proximal end so the second member proximal end extends beyond the first member for protecting the extended needle; and third locking means on the second member at the second member distal end for selectively engaging the first and second locking means in accordance with the axial relative position of the first and second members wherein in the first axial position the first locking means are disengaged from the third locking means by said squeezing said opposing sides.

2. The device of claim 1 wherein the slits are tapered to a wider slit opening at the distal end of the second member.

3. The device of claim 2 wherein the slits remote the distal end terminate in a circular opening.

4. The device of claim 1 wherein the first and second locking means are circumferentially spaced projections extending radially outwardly from the first member outer surface and the third locking means comprises apertures for selectively receiving the projections for axially locking the members together in the first and second positions.

5. The device of claim 4 further including ramp means including fourth locking means on the first member outer surface facing the second locking means in axial spaced relation, the projections forming the first member second locking means being axially adjacent to the proximal end relative to the ramp means, the axial space between the fourth locking means and second locking means for receiving the distal end portion of the first member between the first member end edge and the first locking means.

6. The device of claim 1 further including the needle secured to the first member, the needle comprising first and second needles in which one needle protrudes into the first cavity, the first cavity being dimensioned to receive a vacuum cartridge including a septum to be penetrated by the one needle.

7. The device of claim 6 further including said cartridge assembled to said members and one needle.

8. A needle protective sheath device comprising:
a first cylindrical member having a first cylindrical cavity defining a longitudinal axis, said member having proximal and distal ends, said member having first and second openings on and extending radially transverse the axis in communication with the cavity on the respective distal and proximal ends, the member including connection means at the proximal end opening for securing a hollow needle thereto in communication with the cavity, one end of the needle extending axially beyond the first member proximal end and the other end into said cavity, said member having a pair of opposed axially extending slits in communication with the distal end arranged such that opposing sides of the distal end can be squeezed together at the distal end from a normally spaced apart position to a compressed position;
first locking means on the member outer surface external the cavity on each said opposing sides adjacent to said distal end;
second locking means on the member outer surface external the cavity adjacent to said proximal end;
a second cylindrical member having a second cylindrical cavity defining a second longitudinal axis, said second member having proximal and distal ends, said second member having third and fourth openings on and extending radially transverse the second axis in communication with the second cavity at the respective distal and proximal ends, said second cavity for axially receiving the first member through the third opening with the first and second members in nested concentric relation in a first axial relative position with the members overlying one another with their respective proximal and distal ends adjacent to each other and in a second extended position wherein the second member distal end overlies the first member proximal end so the second member proximal end extends beyond the first member for protecting the extended needle; and
third locking means on the second member at the second member distal end for selectively engaging the first and second locking means in accordance with the axial relative position of the first and second members wherein in the first axial position the first locking means are disengaged from the third locking means by said squeezing said opposing sides.

9. The device of claim 8 wherein the second and fourth openings are of restricted transverse dimension relative to the first and third openings, respectively, such that the first member can not pass through the fourth opening.

10. The device of claim 8 wherein the first and second locking means are circular projections projecting from the first member outer surface and the third and fourth locking means are circular apertures.

11. The device of claim 10 wherein the second member distal end terminates in an edge, said device further including ramp means on the first member outer surface adjacent to the second locking means and forming a fourth locking means between the first and second locking means for engaging the distal edge of the second member.

12. The device of claim 11 wherein the ramp means comprises a plurality of circumferentially spaced axially extending ramps which incline radially away from the first axis in a direction toward to the proximal end, the second member having a like plurality of channels each engaged with a different corresponding ramp.

13. A needle protective sheath device comprising:
a first cylindrical member having an axially extending bore extending therethrough and terminating at distal and proximal end edges of the member, said member having an axially extending slot on opposite sides thereof so the distal end edges can be manually squeezed together;
first locking means on an outer surface of the member adjacent to the distal end;
second locking means on the outer surface adjacent to the proximal end; and
a second cylindrical member having an axially extending bore extending therethrough and terminating at distal and proximal member ends for receiving the first member therein in nested concentric relation, said second member having third locking means at the distal end thereof releasably engaged with the first locking means with said members overlying each other in said nested relation in a first relative position, said third locking means being released from engagement with the first locking means upon said squeezing said distal end edges and for locking engagement with the second locking means in a second relative position wherein the second member extends cantilevered from the first member in a needle protective condition.

14. The device of claim 13 wherein the second member has at least one axially extending channel in the wall forming the bore thereof, the first member including at least one axially extending ramp engaged with the channel, said channel for guiding the ramp in the axial direction, said ramp forming fourth locking means for locking said distal edge of the first member in the axial direction.

15. The device of claim 14 wherein the first and second locking means are projections extending from the peripheral outer surface of the first member and the third locking means is at least one aperture for selectively receiving said projections.

16. The device of claim 15 wherein the projections are circular cylinders and the at least one aperture is circular cylindrical, said channel and ramp for aligning the projections with the at least one aperture.

* * * * *